United States Patent
Park et al.

(10) Patent No.: US 12,403,301 B2
(45) Date of Patent: Sep. 2, 2025

(54) LEAD FOR APPLYING ELECTRICAL STIMULATION TO BODY ORGAN, AND ELECTRODE SYSTEM USING SAME

(71) Applicant: SAMSUNG LIFE PUBLIC WELFARE FOUNDATION, Seoul (KR)

(72) Inventors: Eun Kyoung Park, Seoul (KR); Tae Kyung Kim, Seoul (KR); Min Hee Kang, Seoul (KR); Kyu Sung Lee, Seoul (KR)

(73) Assignee: SAMSUNG LIFE PUBLIC WELFARE FOUNDATION (KR)

( * ) Notice: Subject to any disclaimer, the term of this patent is extended or adjusted under 35 U.S.C. 154(b) by 328 days.

(21) Appl. No.: 17/921,960

(22) PCT Filed: Apr. 1, 2021

(86) PCT No.: PCT/KR2021/004084
§ 371 (c)(1),
(2) Date: Oct. 27, 2022

(87) PCT Pub. No.: WO2021/221326
PCT Pub. Date: Nov. 4, 2021

(65) Prior Publication Data
US 2023/0173259 A1 Jun. 8, 2023

(30) Foreign Application Priority Data
Apr. 28, 2020 (KR) .................. 10-2020-0051334

(51) Int. Cl.
*A61N 1/05* (2006.01)
*A61N 1/36* (2006.01)
*A61N 1/375* (2006.01)

(52) U.S. Cl.
CPC ....... *A61N 1/0534* (2013.01); *A61N 1/36125* (2013.01); *A61N 1/36128* (2013.01); *A61N 1/37514* (2017.08)

(58) Field of Classification Search
CPC .............. A61N 1/0534; A61N 1/36125; A61N 1/36128; A61N 1/37514; A61N 1/056;
(Continued)

(56) References Cited

U.S. PATENT DOCUMENTS 7,181,288 B1 * 2/2007 Rezai ................... A61N 1/0534
607/116
8,224,456 B2 * 7/2012 Daglow ............... A61N 1/0551
607/116
(Continued)

FOREIGN PATENT DOCUMENTS

| JP | 2007-202727 A | 8/2007 |
| KR | 10-1033749 B1 | 5/2011 |
| KR | 10-2020-0016103 A | 2/2020 |

OTHER PUBLICATIONS

International Search Report of WIPO in Application No. PCT/KR2021/004084, filed Apr. 1, 2021.

*Primary Examiner* — Carl H Layno
*Assistant Examiner* — Anh-Khoa N Dinh
(74) *Attorney, Agent, or Firm* — Dilworth IP, LLC

(57) ABSTRACT

A lead implanted in a body to apply electrical stimulation to body organs includes an electrode wire having one end provided as an insertion portion to be inserted into a body and another end provided as an interface portion for connection with an external device; a first electrode in the insertion portion to transmit electrical stimulation to body organs; a second electrode on the interface portion to receive electrical stimulation applied from outside; a signal line that interconnects the first electrode and second electrode to transmit electrical stimulation received by the second elec-
(Continued)

trode to the first electrode; and a ring member that covers the first electrode and has an opening for exposing the first electrode in a portion of a circumferential direction, and is mounted to be movable in a longitudinal or circumferential direction with respect to the electrode wire by an external force to adjust an exposure position of the first electrode.

11 Claims, 8 Drawing Sheets

(58) Field of Classification Search
CPC ........ A61N 1/3752; A61N 1/05; A61N 1/372; A61N 1/0551; A61N 2001/0578; A61N 1/0492; A61N 1/0472; A61N 1/0529; A61N 1/0539; A61N 1/375; A61N 1/0408; A61N 1/0476; A61N 1/0531; A61N 1/0587; A61N 1/36564; A61N 1/36139; A61N 1/06; A61N 1/0558; A61N 1/04; A61N 1/3603; A61N 1/328; A61N 1/36542; A61N 1/3655; A61N 1/36557; A61N 1/368; A61N 1/40; A61N 1/059; A61B 2018/143; A61B 2018/1432; A61B 2018/144; A61B 2090/062; A61B 2090/08021; A61B 2090/363; A61B 2090/3966; A61B 34/25; A61B 34/32; A61B 34/37; A61B 5/02; A61B 5/021; A61B 5/061; A61B 6/485
See application file for complete search history.

(56) References Cited

U.S. PATENT DOCUMENTS

| | | | |
|---|---|---|---|
| 2004/0082850 A1* | 4/2004 | Bonner | A61B 5/06 600/424 |
| 2006/0217779 A1 | 9/2006 | Ransbury et al. | |
| 2010/0268298 A1* | 10/2010 | Moffitt | A61N 1/36182 607/45 |
| 2010/0331938 A1* | 12/2010 | Sommer | A61N 1/0534 607/116 |
| 2011/0313500 A1* | 12/2011 | Barker | A61N 1/0534 607/116 |
| 2014/0243922 A1* | 8/2014 | Haessler | A61M 5/14276 607/138 |

* cited by examiner

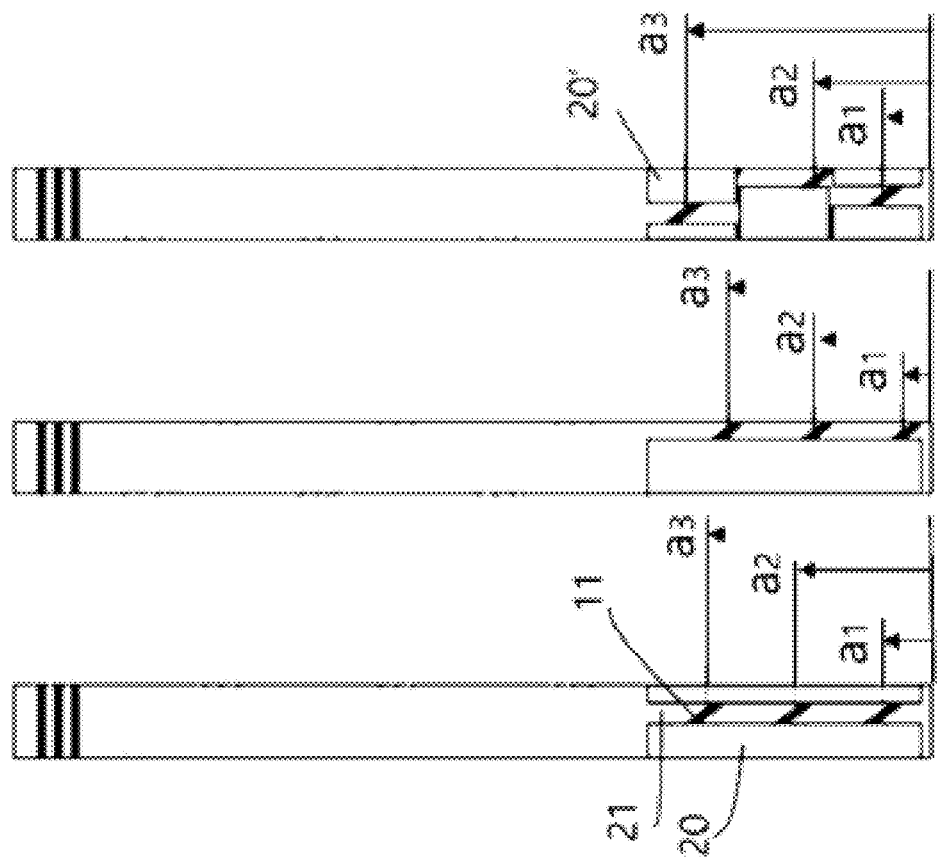

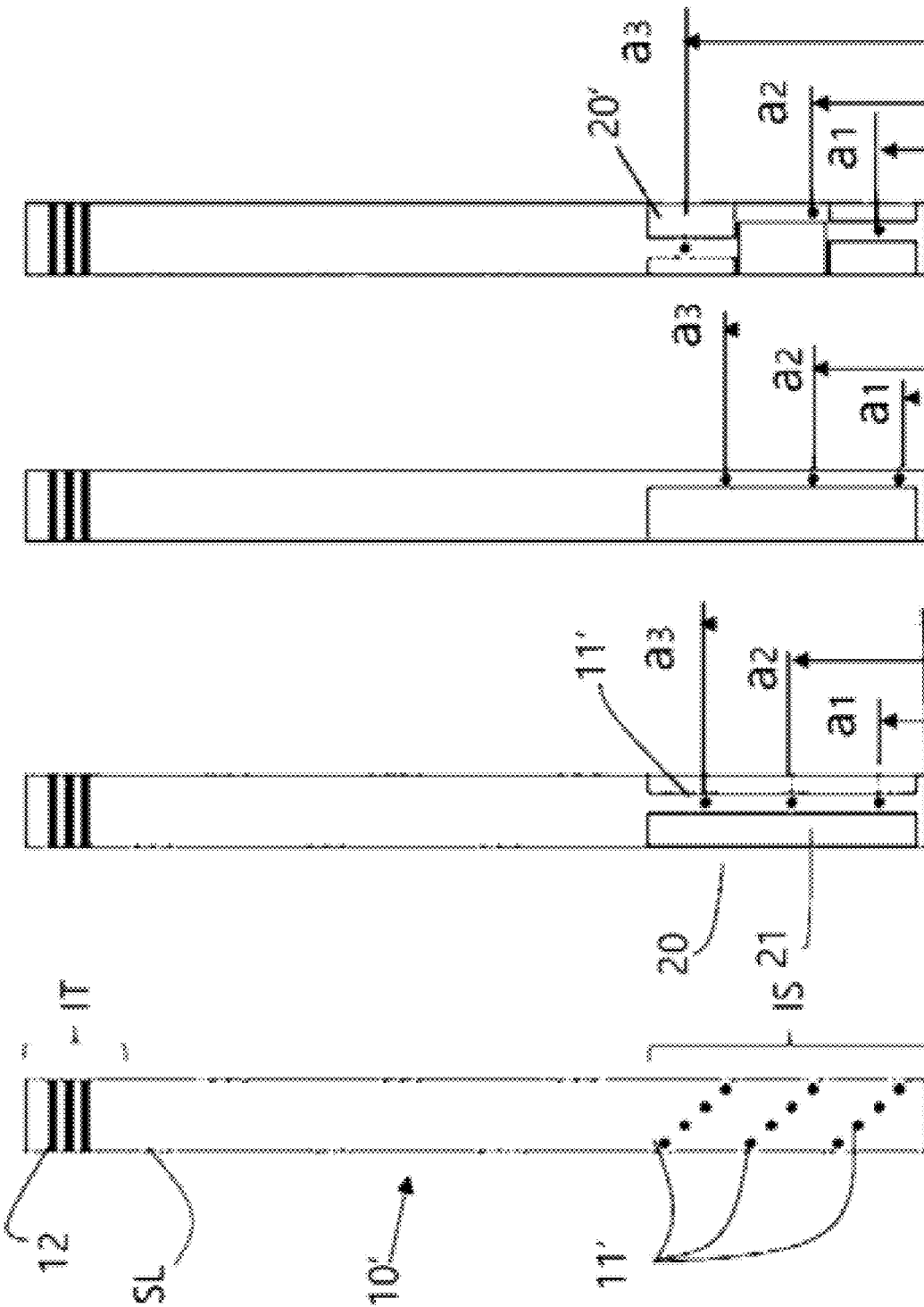

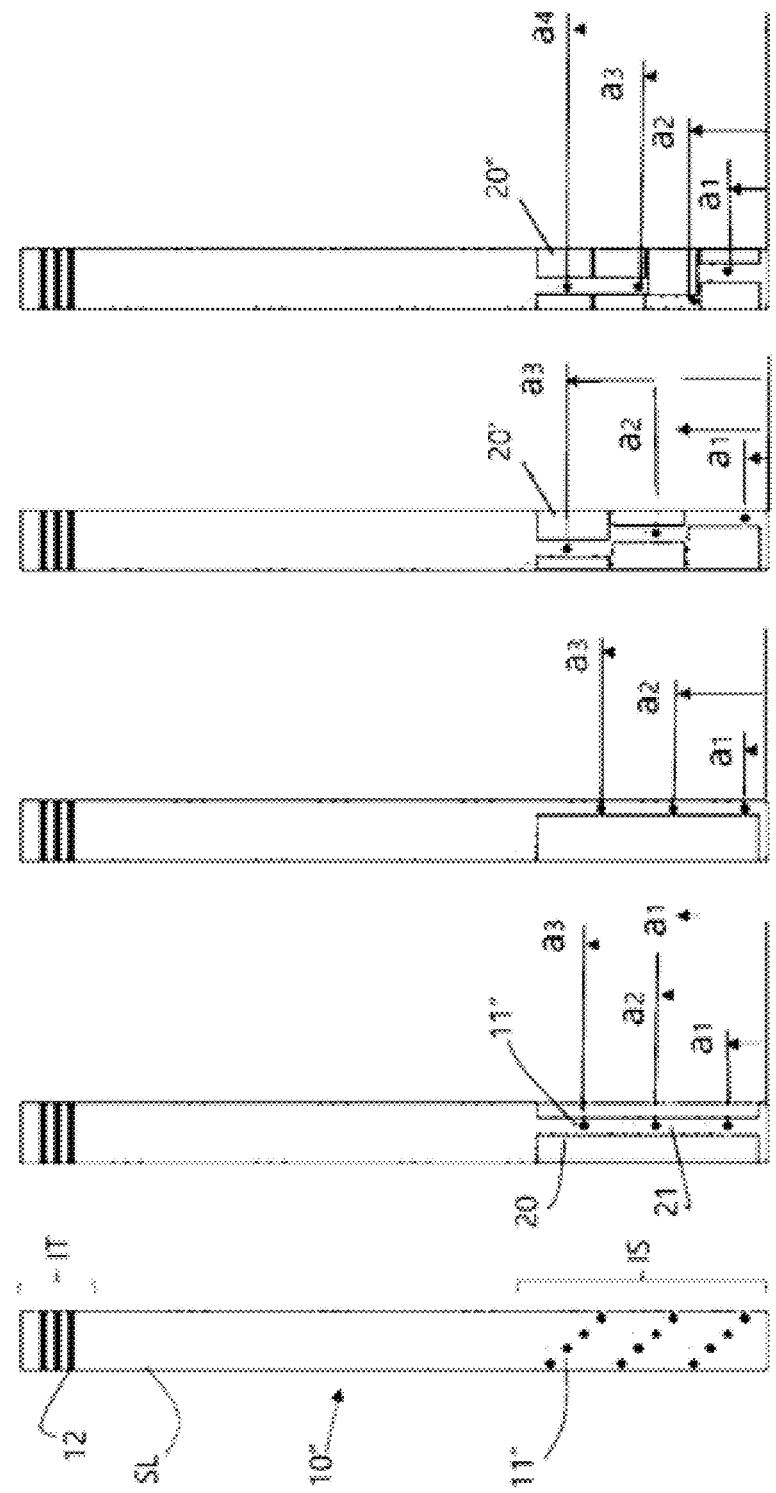

LEAD FOR APPLYING ELECTRICAL STIMULATION TO BODY ORGAN, AND ELECTRODE SYSTEM USING SAME

FIELD OF THE INVENTION

The present invention relates to a lead for applying electrical stimulation to body organs and a lead system using the same.

BACKGROUND OF THE INVENTION

Due to the complexity of modern society, modern people are easily exposed to accidents or diseases and lose their intrinsic functions or exercise abilities, but there is a limit to healing these patients with medicine alone. In order to overcome these limitations, the field of biomedical engineering, which was created by grafting the technology of the engineering field with the medical field, is developing, and as a result, major changes are occurring in many areas of a health care system.

For example, pacemakers and ventricular defibrillators are saving many lives and playing an innovative role in the treatment of heart disease. In addition, using pacemaker technology, the surgeon implants a Deep Brain Stimulation (DBS) device into the patient's brain to control an abnormal brain function (e.g., see patent documents).

Abnormal physical behavior or mental disorders result from abnormal functions of the brain, such as Parkinson's Disease (PD) or Obsessive-Compulsive Disorder (OCD). PD is a chronic degenerative brain disease in which the main symptoms are trembling hands and feet, slow movements, and stiff muscles, and OCD is a mental disorder in which people are reluctant to go out because of fear that they may be contaminated by things they come in contact with.

Neurosurgeons are now using deep brain stimulators to treat serious health problems such as Parkinson's disease, obsessive-compulsive disorder and depression. A treatment method using a deep brain stimulator is a surgical method, and it is the only hope for treating obsessive-compulsive disorder and is evaluated as a method that has been proven effective in curing Parkinson's disease.

Deep brain stimulation utilizes implantable medical devices to deliver accurate electric pulses. A deep brain stimulator is largely composed of an implantable pulse generator, an extension, and a lead.

In general, when an implantable pulse generator is implanted under the chest subcutaneously, a lead is placed deep in a specific region of the brain, and the two components are connected to each other with an extension to generate stimulation through the implantable pulse generator, the stimulation is transmitted to the lead through the extension, and microelectrical stimulation may be applied to the specific region of the brain through the lead.

It is important to check the position and contact point of the lead after surgery because the clinical course may differ for each patient depending on the position of the lead. Accordingly, in lead implantation surgery, the optimal stimulation position is found by detecting brain signals from several small-sized electrodes using a micro-lead to select the position of stimulation.

However, In the case of micro-lead, it is not suitable for stimulation because the micro-lead is small, so surgery is performed to remove the micro-lead and reinsert a lead for stimulation. During reinsertion of the lead for stimulation, it is not easy to insert the lead for stimulation according to a target precisely found because the position of the lead for stimulation is different from that of the existing micro-lead and the size of a recording area is different.

SUMMARY OF THE INVENTION

The present invention provides a lead that is inserted into the body without using a micro-lead and configured to adjust the size and position of a contact point of leads that apply electrical stimulation, and a lead system using the lead.

As an embodiment of the present disclosure, a lead may be provided.

The lead according to an embodiment of the present disclosure may include: an electrode wire having one end provided as an insertion portion to be inserted into a body and the other end provided as an interface portion for connection with an external device; a first electrode in the insertion portion to transmit electrical stimulation to body organs; a second electrode on the interface portion to receive electrical stimulation applied from outside; a signal line that interconnects the first electrode and the second electrode to transmit electrical stimulation received by the second electrode to the first electrode; and a ring member that covers the first electrode and has an opening for exposing the first electrode in a portion of an circumferential direction, and is mounted to be movable in a longitudinal or circumferential direction with respect to the electrode wire by an external force to adjust an exposure position of the first electrode.

The lead according to an embodiment of the present disclosure may further include the ring member comprises an insulating material or a conductor.

The lead according to an embodiment of the present disclosure may further include the ring member is movable with respect to the electrode wire by a magnetic force acting from outside.

The lead according to an embodiment of the present disclosure may further include a gap between openings of the ring member is adjusted by an external force.

The lead according to an embodiment of the present disclosure may further include the first electrode extends obliquely along an outer surface of the electrode wire in the insertion portion.

The lead according to an embodiment of the present disclosure may further include a plurality of first electrodes are arranged in a form of point electrodes on an outer surface of the electrode wire in the insertion portion.

The lead according to an embodiment of the present disclosure may further include a plurality of ring members are provided and arranged adjacent to each other in a longitudinal direction at the insertion portion of the electrode wire.

The A lead system implanted in a body to apply electrical stimulation to body organs according to an embodiment of the present disclosure may include: a main processor connected to an external device for communication and control; one or more leads implanted in a body to apply electrical stimulation to body organs and configured according to any one of claims 1 to 7; an electrode clamp for electrical connection with the lead; and a lead operating mechanism for inserting, removing and rotating the lead, the lead operating mechanism including a manual operation member configured to be manually operated by a controller or operator driven according to a control signal from the main processor, wherein the lead comprises: an electrode wire having one end provided as an insertion portion to be inserted into a body and the other end provided as an interface portion for connection with an external device; a plurality of first electrodes in the insertion portion to transmit electrical stimulation to body organs; a plurality of second electrodes on the interface portion to receive electrical stimulation applied from outside; a plurality of signal lines that interconnect the first electrodes and the second electrode respectively to transmit electrical stimulation received by the second electrode to the first electrode; a ring member that covers the first electrode and has an opening for exposing the first electrode in a portion of an circumferential direction, and is mounted to be movable in a longitudinal or circumferential direction with respect to the electrode wire by an external force to adjust an exposure position of the first electrode; and a guide wire inserted into an inner space of the electrode wire to support the electrode wire when the electrode wire is inserted into a brain region.

The lead system according to an embodiment of the present disclosure may further include the controller comprises: a driving element driven according to a control signal from the main processor; and an operation key driven in an extension direction and a circumferential direction of the lead by the driving element, one end disposed adjacent to the ring member, and having a magnetic force, wherein the one end of the operation key is magnetized by application of electric power to apply a magnetic force to the ring member to move and rotate the ring member.

The lead system according to an embodiment of the present disclosure may further include the operation key is at a position of the guide wire of the lead, and is arranged to be inserted into the position of the guide wire in a state in which the guide wire is removed.

The lead system according to an embodiment of the present disclosure may further include the manual operation member comprises: a main body extending in a longitudinal direction of the lead; an operation unit provided on an upper end of the main body and applied with an operating force by an operator; and a press unit that is expanded by the operating force applied to the operation unit, wherein the press unit is arranged between openings of the ring member and expanded by the operating force to expand the openings.

The lead system according to an embodiment of the present disclosure may further include the manual operation member is a case member configured to surround the lead in a cylindrical shape with both ends open, wherein a male screw is formed on the ring member, and a female screw is formed at a position in contact with the ring member in the case member, so that the case member and the ring member are screwed together.

The lead system according to an embodiment of the present disclosure may further include: when the case member is rotated in a first direction, the case member is screwed with the ring member to rotate the ring member in the first direction to adjust a position of the ring member in the circumferential direction with respect to the lead. and when the case member is rotated in a second direction opposite to the first direction, the screw coupling between the case member and the ring member is released to separate the case member.

According to the present invention, it is possible to reduce the conventional secondary lead insertion process of micro-lead insertion and lead insertion to one time, and it is possible to easily adjust the size and position of a contact point of leads.

BRIEF DESCRIPTION OF DRAWINGS

FIGS. 2A, 2B, 2C, 2D and 2E schematically show an external structure of the lead A according to a first embodiment of the present invention.

FIGS. 3A, 3B, 3C and 3D schematically show an external structure of the lead A according to a second embodiment of the present invention.

FIG. 4A, 4B, 4C, 4D and 4E schematically show an external structure of the lead A according to a third embodiment of the present invention.

DETAILED DESCRIPTION OF THE INVENTION

Hereinafter, embodiments of the present invention will be described with reference to the drawings. In the following description, descriptions of a well-known technical configuration in relation to a lead implantation system for a deep brain stimulator will be omitted. For example, descriptions of the configuration/structure/method of a device or system commonly used in deep brain stimulation, such as the structure of an implantable pulse generator, a connection structure/method of the implantable pulse generator and a lead, and a process for transmitting and receiving electrical signals measured through the lead with an external device, will be omitted. Even if these descriptions are omitted, one of ordinary skill in the art will be able to easily understand the characteristic configuration of the present invention through the following description.

Figure 1:
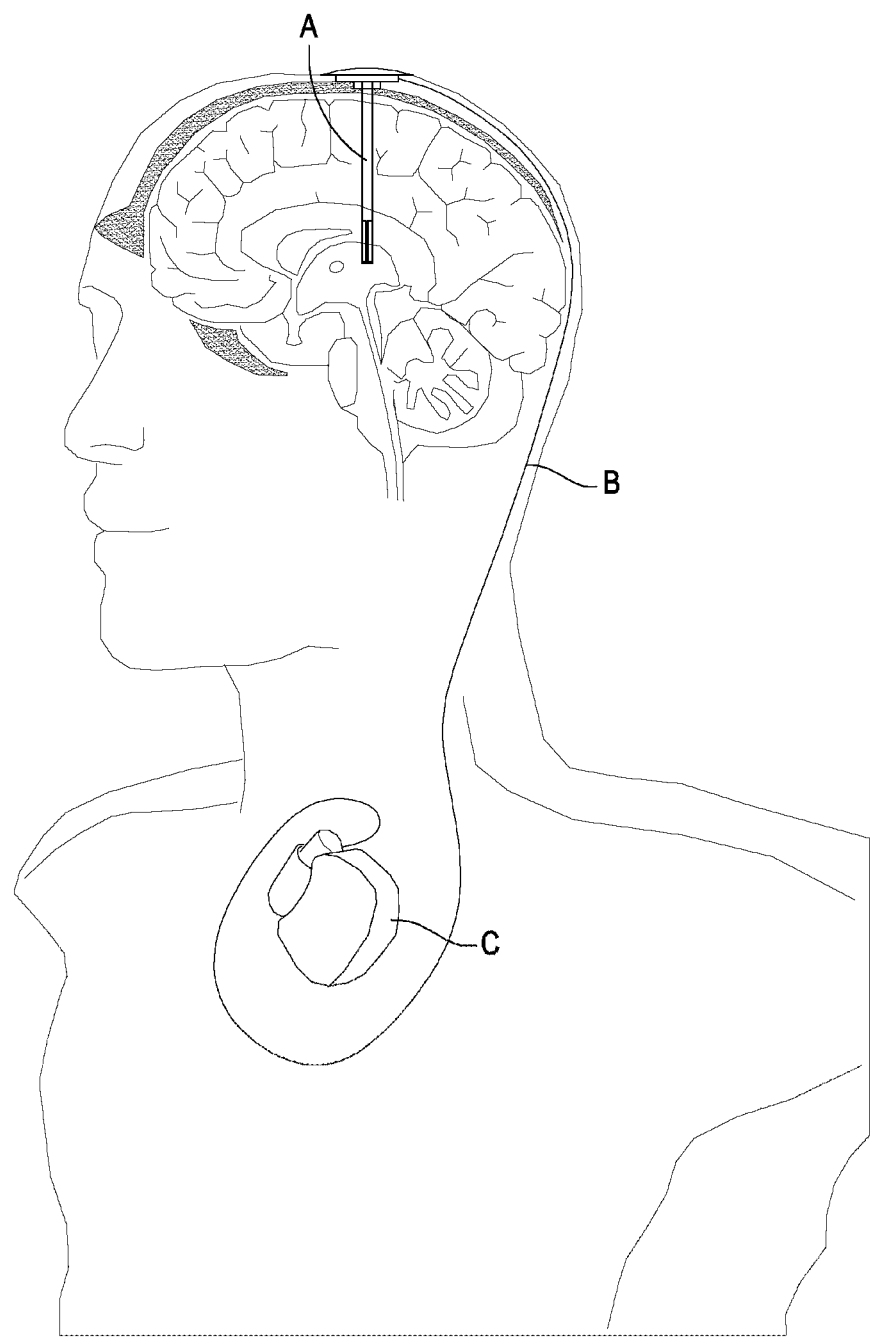
FIG. 1 schematically shows a state in which a deep brain stimulator targeted by the present invention is applied to the body.

FIG. 1 schematically shows a state in which a deep brain stimulator targeted by the present invention is applied to the body. As shown, the deep brain stimulator includes a plurality of leads A (only one is shown in FIG. 1) implanted in a specific region of the brain, an implantable pulse generator C implanted subcutaneously in the chest, and an extension connecting the leads to the implantable pulse generator. When stimulation is generated through the implantable pulse generator, the stimulation is transmitted to a lead through an extension, and micro-electrical stimulation may be applied to a specific region of the brain through the lead.

The present invention relates to a lead implantation system for a deep brain stimulator that enables implantation of a lead A from among components of the deep brain stimulator into a target in a specific region of the brain accurately and with a simple procedure, and a lead. Accordingly, as described above, descriptions of an implantable pulse generator, an extension, a connection structure/method of a lead and an extension, and an operation of a deep brain stimulator including an implantable pulse generator, which do not constitute the features of the present invention, will be omitted.

FIGS. 2A and 2B schematically show an external structure of the lead A according to a first embodiment of the present invention.

As shown, the lead A of the first embodiment includes an electrode wire 10 (as shown in FIG. 2A) that transmits a stimulation signal from the brain region into which a lead is inserted, a C-ring 20 as a ring member (as shown in FIG. 2B), provided as a lower portion of the electrode wire in the drawing, covering an insertion part to be inserted into the brain region, and mounted slidably in a circumferential direction or in a longitudinal direction with respect to the electrode wire according to an external force, and although not specifically illustrated, a guide wire (not shown) that is inserted into an inner space of the electrode wire and supports the electrode wire when the electrode wire is inserted.

In addition, a signal line SL extending spirally between an interface portion IT above the electrode wire and an insertion portion IS under the electrode wire to interconnect the first and second electrodes 11 and 12 provided at both ends of the electrode wire is also provided.

In the FIG. 2A, the signal line SL is wound and fixed to the outside of the electrode wire in a spiral form, but the present invention is not particularly limited to the shape of the signal line.

In other words, as long as the signal line is connected to electrodes provided at upper and lower ends of the electrode wire, the signal line is not limited to a shape fixed to a surface of the electrode wire 10 spirally, and may be fixedly inserted into the electrode wire 10 spirally.

In addition, the first and second electrodes 11 and 12 are also not limited as shown in the drawing, and may be provided on the electrode wire 10 in various forms, particularly in relation to the C-ring 20. The electrode wire 10 is flexible and has excellent durability, and is formed of a material harmless to the human body, for example, polyurethane.

The C-ring 20 of FIG. 2B constituting one feature of the present invention is formed of an insulating material or a conductor according to a specific use. In an embodiment shown in FIGS. 2C and 2D, the C-ring is formed in a cylindrical shape, and a portion in a circumferential direction is cut to form an opening 21. The C-ring is disposed to cover the first electrode 11 at a lower end, and the first and second electrodes 11 and 12 are exposed through the opening.

When the C-ring includes an insulating material, the C-ring prevents exposure of a lower electrode covered by the C-ring, and at the same time, the electrode is exposed through the opening 21 so that stimulation may be performed only at a desired brain region.

On the other hand, when the C-ring includes a conductor, the C-ring increases a cross-sectional area of an electrode covered by the C-ring, and electrical stimulation may be performed by broadly expanding the stimulation of the brain region from point stimulation to surface stimulation.

In addition, as shown in FIGS. 2C, 2D and 2E, the C-ring may be used by appropriately selecting its size. That is, a single C-ring covering the entire lower portion of an electrode wire may be used (see FIGS. 2C and 2D), or a plurality of C-rings (see FIG. 2E) including an insulating material and a conductor may be used according to the patient's condition.

Although not specifically shown in the figures, the C-ring is also in the form of a hollow having a certain thickness (only part of the C-ring is removed, so that the C-ring has a C-shaped cross section in a plan view), like the electrode wire, so that a mobile clamp, which will be described later, is inserted between the removed part, and the interval may be adjusted using the mobile clamp.

On the other hand, although not shown, the electrode wire 10 is hollow in the longitudinal direction, and a guide wire is inserted therein, gives rigidity to the entire electrode wire during electrode insertion, and is removed after the insertion of the electrode wire is completed. According to an embodiment, the guide wire is sometimes separated for insertion and rotation of the C-ring after the insertion of the electrode wire, or removed at the final stage of the electrode insertion.

Action of adjusting a position, etc. where stimulation is applied by the first electrode 11 using the C-ring 20 and a configuration related to such action will be described with reference to leads of first to third embodiments shown in FIGS. 2A to 2E, 3A to 3D and 4A to 4E, respectively.

In a lead of an embodiment of the present invention, the second electrode 12 is provided with three electrodes parallel to each other in the longitudinal direction and arranged on a plane perpendicular to an axial direction of the lead 10, but in the lead of the first embodiment shown in FIGS. 2A to 2E, the first electrode 11 has three strip-shaped electrodes parallel to each other and spirally arranged.

The C-ring 20 includes an insulating material and selectively exposes a portion of the first electrode 11 through the opening 21 to transmit stimulation to the brain.

When the C-ring is rotated, the position of the first electrode 11 exposed through the opening 21 is changed and the first electrode 11 is formed to be inclined. As shown in FIG. 2C and FIG. 2D, exposed positions of respective electrodes constituting the first electrode 11 are different. In other words, distances at a2, and a3 from the bottom of the electrode wire 10 to respective electrodes are different as the electrodes are rotated.

Accordingly, by rotating the C-ring 20 to change a position of the opening 21 in a circumferential direction, a position at which the electrode is exposed may be adjusted to change a position at which stimulation is applied to the brain.

On the other hand, as shown in FIG. 2E, three C-rings 20 having a short length may be provided and arranged adjacent to each other in the longitudinal direction of the electrode wire 10. Because each C-ring 20' may be rotated to adjust its position in a circumferential direction of an opening, a position where an electrode is exposed by the opening of each C-ring, that is, a position indicated by a distance from the bottom of the electrode wire in the drawing, may be adjusted.

According to this method, by individually adjusting the position of each electrode constituting the first electrode 11, it is possible to finely adjust a portion to which stimulation is applied by the electrode.

Next, a lead of the second embodiment will be described with reference to FIGS. 3A to 3D.

In the lead of FIG. 3A, a first electrode 11' is configured in the form of point electrodes discontinuously arranged in a circle, unlike a first electrode of the first embodiment. The electrodes constituting the first electrode 11' are arranged along three signal lines inclined parallel to each other.

By rotating the C-ring 20, electrodes that are exposed to stimulate the brain may vary. As shown in FIGS. 3B and 3C, according to the rotation of the C-ring, the position of the opening 21 in the circumferential direction is changed, so that the distances a1, a2, and a3 from the bottom surface of the electrode wire to the exposed electrodes are changed. Accordingly, by rotating the C-ring, the position of an exposed electrode may be adjusted according to the brain region to be stimulated by the first electrode 11.

As can be seen in FIG. 3D, as in the first embodiment, by arranging a plurality of short C-rings to individually control positions of respective exposed electrodes, a portion to which stimulation is applied by an electrode may be finely adjusted.

Next, a lead of the third embodiment will be described with reference to FIGS. 4A to 4E.

In a lead of an embodiment of he present invention, three mutually parallel signal lines SL are spirally extended from three electrodes constituting the second electrode 12. In the third embodiment, the three signal lines extend to a lower end of the insertion portion IS, and a first electrode 11" in the form of point electrodes connected to each signal line to which electrical stimulation is applied is disposed on an outer surface of an electrode wire.

In the lead of the second embodiment, the point electrodes constituting the first electrode 11" are spirally arranged along respective signal lines. However, in the third embodiment, electrodes are arranged in such a way that electrodes connected to respective signal lines are adjacent to each other and are spirally arranged.

According to this configuration, electrodes exposed through the opening 21 of the C-ring may be arranged in various ways.

As shown in FIGS. 4B and 4C, the electrodes arranged through the opening of the C-ring may be differently connected to signal lines connected to electrodes constituting the second electrode 12 according to the position of the opening 21. In addition, the distance a1, a2, a3 from the bottom of the electrode wire 10 may be adjusted.

By adjusting the frequency, voltage or current of electrical stimulation applied to electrodes of the second electrode 12 to which respective signal lines SL are connected differently, and adjusting the position of the opening 21 of the C-ring, a position at which electrical stimulation is applied to the brain or the frequency of the electrical stimulation may be adjusted by electrodes exposed through the opening.

In addition, as shown in FIGS. 4D and 4E, several short C-rings 20' and 20", such as three or four, may be arranged in a longitudinal direction.

Accordingly, by adjusting the position of an opening of each C-ring, the position to which electrical stimulation is applied and the frequency, current and voltage of applied electrical stimulation may be very finely adjusted.

As described above, in a lead according to embodiments of the present invention, by arranging the C-ring 20 having an opening to surround the insertion portion IS of an electrode wire and adjusting a circumferential position of the opening 21, a position at which electrical stimulation is applied to the brain or electrical stimulation may be finely adjusted and changed.

Hereinafter, a configuration for arranging a C-ring on a lead and adjusting the position will be described.

Figure 5A:
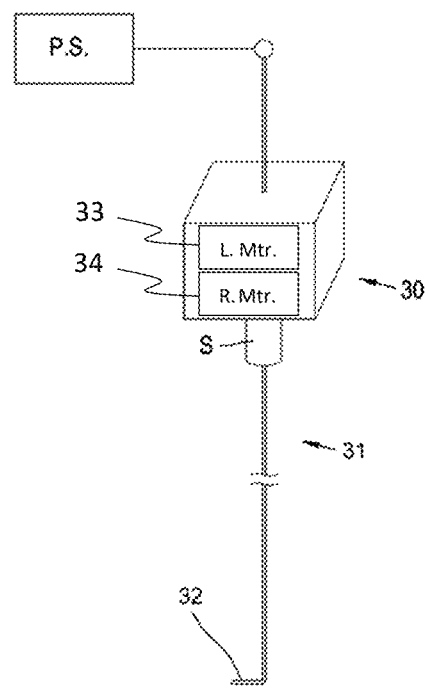
FIGS. 5A and 5B show a schematic structure of a C-ring controller used in one embodiment of the lead system of the present invention.

FIG. 5A shows a schematic structure of a C-ring controller used in one embodiment of the lead system of the present invention. That is, the lead system of the present invention includes a main processor in charge of communication and control, an electrode clamp for electrical connection with an electrode of the lead, and a C-ring controller 30 capable of moving/rotating a C-ring.

The main processor is connected to a separate external device (PC, tablet, smartphone, etc.) to exchange signals, digitizes an electrical signal measured by an electrode, transmits the electrical signal to the external device, or receives a control signal from the external device to drive a motor.

The electrode clamp has a semicircular structure attached to an end of a clamp with a spring so that the electrode clamp may be well attached to a surface of a lead. In the electrode clamp, the lead comes out of a contact point located on one arm of the clamp and is connected to the main processor, and a guide line is attached to the opposite arm to align positions of the lead and the clamp.

The main processor and the electrode clamp are known components commonly used in the field of deep brain stimulation, and a description thereof will not be given herein.

The C-ring controller 30 includes a linear motor (L. Mtr.) 33 and a rotary motor (R. Mtr.) 34 moving by receiving a control signal from the main processor, and an operation key 31 made of a metal plate is attached to a motor shaft, so that the electrode wire may be moved in a longitudinal direction and rotated about an axis according to driving of the linear motor 33 and the rotary motor 34.

Figure 5B:
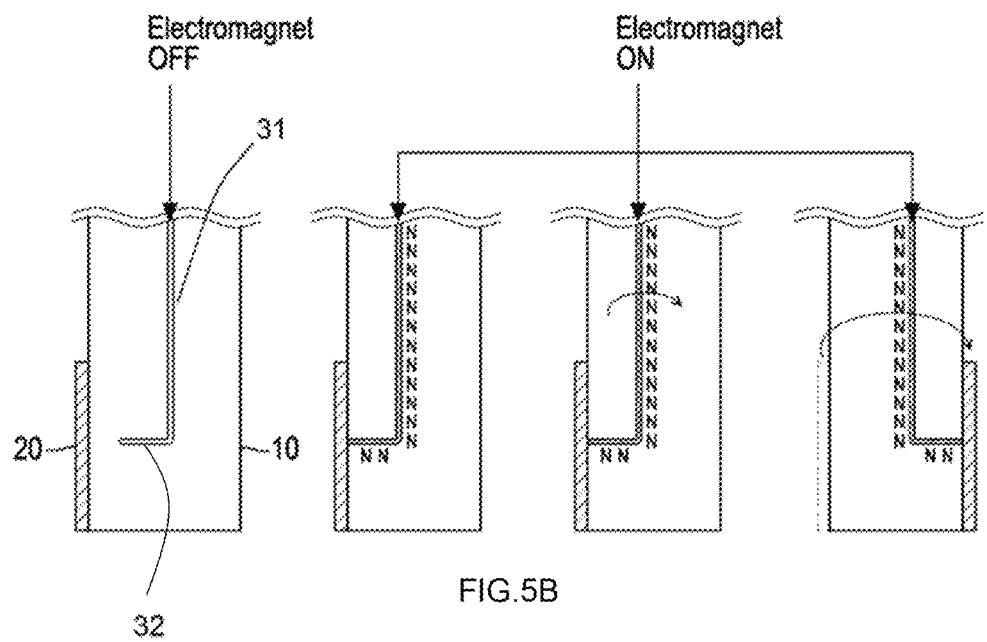

That is, as shown in FIGS. 5A and 5B, the operation key 31 is movably and rotatably mounted on a support S of the C-ring controller 30, one end of which is connected to a power supply P.S., and the other end 32 is bent. When power is applied through the power supply, the bent end 32 of the operation key is magnetized, and attractive force is applied between the end 32 and the C-ring 20 by magnetic force, so that the C-ring 20 is moved and rotated by movement and rotation of the operation key 31.

Hereinafter, a detailed operation of inserting the C-ring configured as described above or adjusting the position of the C-ring will be described.

First, a deep brain stimulation operator (hereinafter referred to simply as 'operator') applies power to a lead system for a deep brain stimulator (not shown) and performs an initialization process (communication connection with an external device for control). Next, the operator inserts the electrode wire 10 into a specific region of the brain in a state in which the electrode wire 10 is inserted into a guide wire according to a conventional lead insertion sequence.

Next, the operator removes the guide wire, places the C-ring controller 30 in accordance with a hollow hole of the lead A from which the guide wire is removed, and connects the C-ring controller to a control unit (not shown) of the lead system for a deep brain stimulator.

On the other hand, the operator opens an electrode clamp, closes the electrode clamp according to a guide line, and connects an electrode contact of the electrode clamp to an electrode so that the electrode contact is in contact with the electrode in a correct position. This process is performed for a plurality of (e.g., three) leads. The operator transmits a neural signal obtained from an electrode portion of each electrode wire to the control unit in real time, and calculates which point of the electrode is closest to a target.

Next, the operator determines the shape and number of C-rings to be inserted according to the calculated point, and whether they are conductors or non-conductors.

The C-ring may be inserted and fastened together with an electrode wire when the electrode wire is inserted, but may be inserted later by the following two methods.

Figure 6:
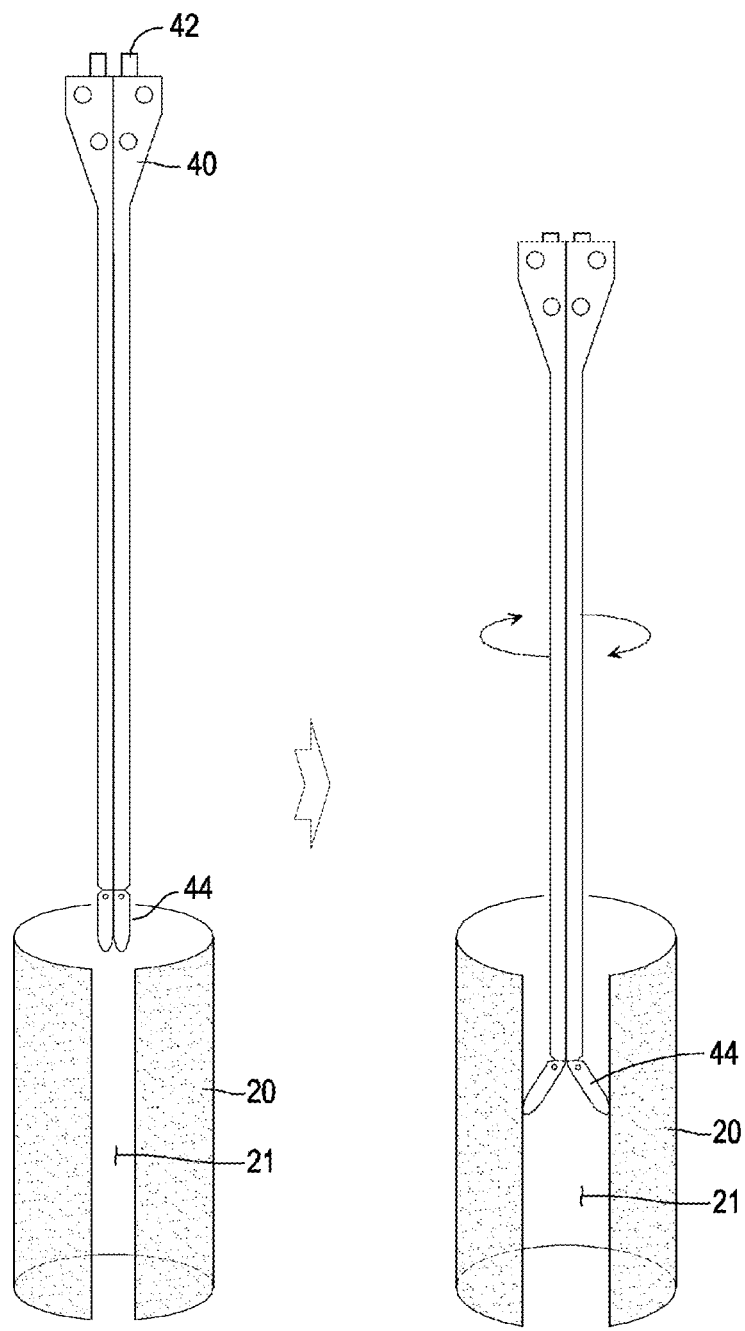
FIG. 6 schematically shows a schematic structure of a mobile clamp used in the lead and a fastening structure with the C-ring according to an embodiment of the present invention.
Figure 7:
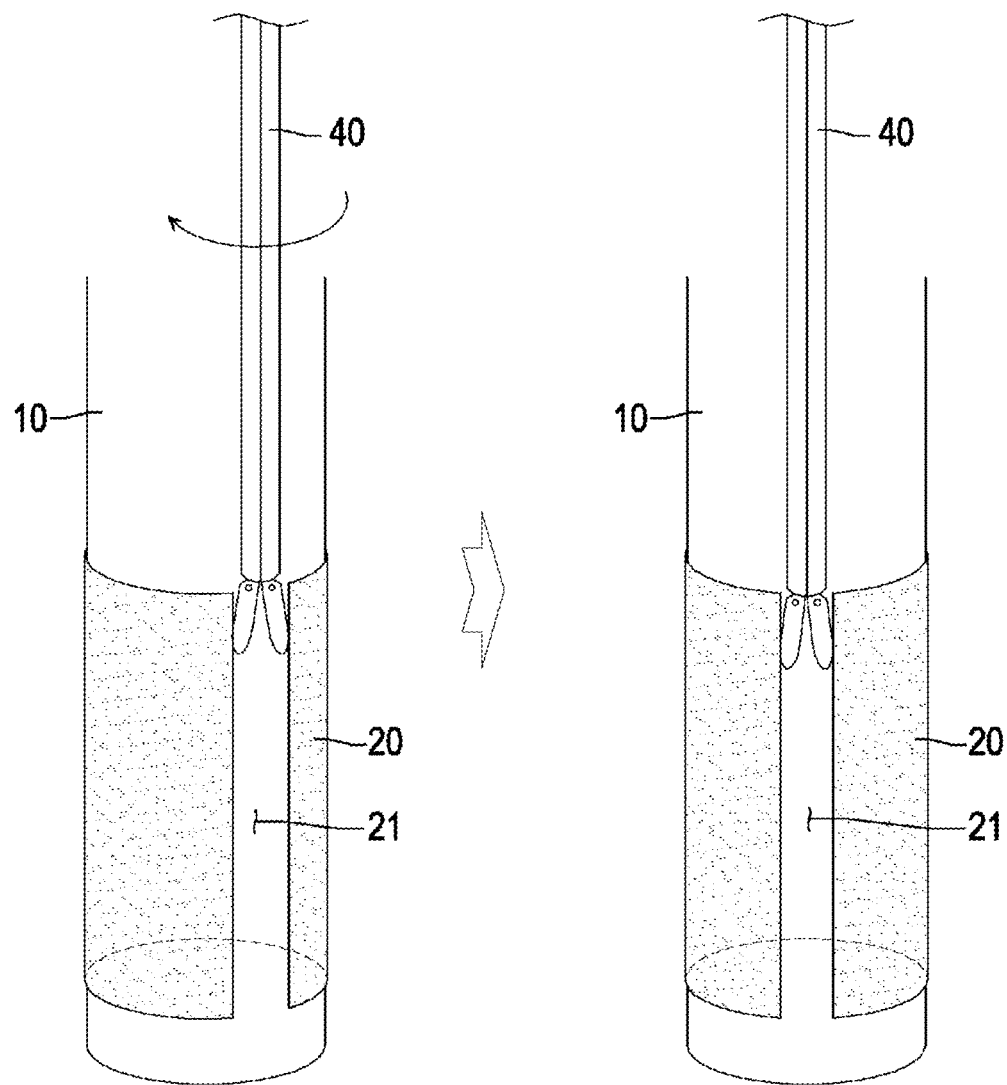
FIG. 7 schematically shows a schematic structure of a change in the position of the C-ring fastened to the lead using a moving clamp of FIGS. 4a and 4b.

The operator inserts a C-ring by using a mobile clamp 40 provided as a manually operated member shown in FIG. 6.

A pair of buttons 42 is provided at an upper end of the mobile clamp as an operation unit, and a pair of pressing elements 44 provided as a press unit that open and close according to the operation of the button are provided at a lower end of the mobile clamp.

That is, when the operator presses a button 42, a pressing element 44 expands and contact an inner circumferential surface of an opening of the C-ring to expand the opening, and when the operator presses the button again, the expanded state may be released, i.e., retracted. The operator inserts the mobile clamp 40 into the opening of the C-ring determined through the above process, and then presses the button 42 so that the pressing element 44 expands both sides of the opening of the C-ring.

Accordingly, the C-ring may be inserted from the outside of an electrode wire with a diameter that is sufficiently greater than that of the electrode wire. When the C-ring is inserted and a target point is reached, the operator presses the button 42 again to retract the expanded pressing element, and the C-ring is retracted and held in place while surrounding an electrode wire 20.

This operation is not limited only to the insertion of the C-ring, and as shown in FIGS. 5A and 5B, may be used to adjust longitudinal and circumferential positions of the C-ring and the opening with respect to the electrode wire after inserting the C-ring.

A method of adjusting the position of the C-ring using the C-ring controller 30 will be described with reference to FIGS. 5A and 5B. In the following description, the C-ring is made of a non-conductor and stimulation is applied to a portion of the first electrode 11 exposed through the opening 21.

The C-ring 20 is disposed to cover the inserted first electrode 11 of the electrode wire 10 by the operation as described above, and the opening 21 of the C-ring needs to be located at a position where stimulation is to be applied. This operation is performed by adjusting the position of a tip 32 of the operation key 31 by the C-ring controller 30.

When power is applied to the operation key 31 to magnetize the tip 32, the C-ring facing the tip is coupled to the tip of the operation key 31 by magnetic force. In this state, by rotating the operation key 31 by the C-ring controller 30, the opening 21 of the C-ring is located at a target position, and an electrode is exposed by the opening 21 to apply stimulation to the brain.

In the case of an embodiment in which a plurality of C-rings 20 are arranged in the longitudinal direction of the electrode wire, the operation key 31 may adjust the position of one C-ring, and may move in the longitudinal direction to adjust the position of the other C-ring. In this way, the positions of the plurality of C-rings are adjusted by one operation key.

After adjusting the position of the C-ring and applying a stimulation signal through an electrode, the operator may determine whether stimulation is applied to a target position from an obtained neural signal, and then adjust the position of the C-ring again.

After the position adjustment is completed, the C-ring controller 30 and the operation key 31 are removed from the electrode wire 10.

Figure 8:
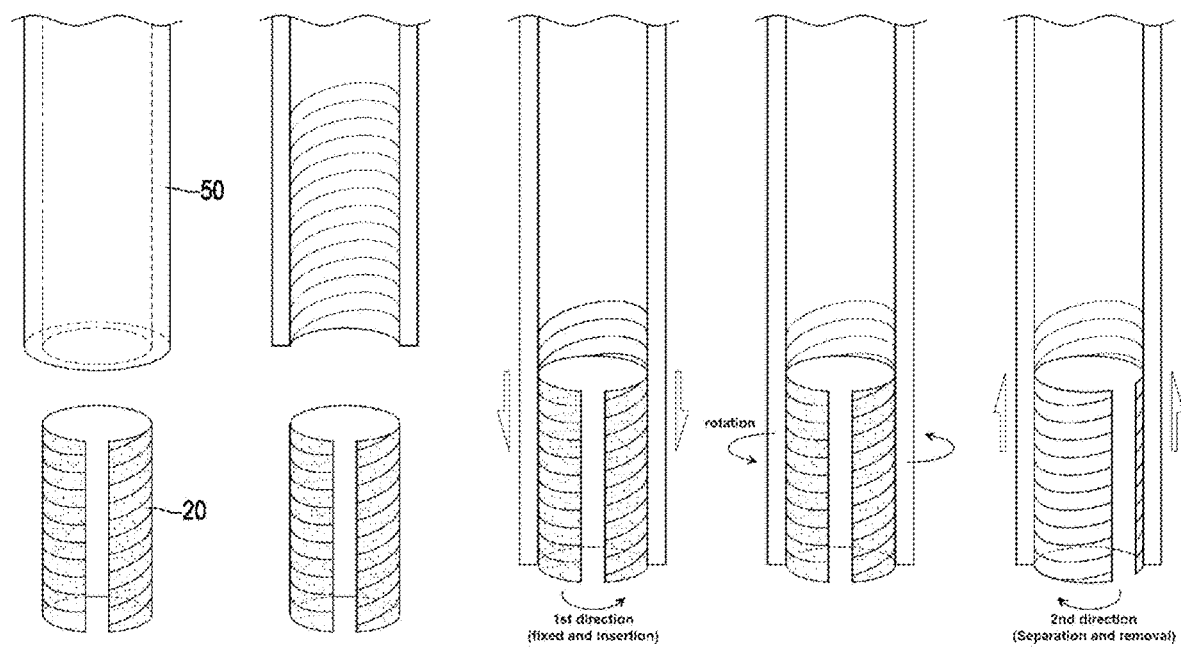
FIG. 8 schematically shows a coupling and separation of a moving case and a C-ring used in a lead A according to an embodiment of the present invention.

In addition, as shown in FIG. 8, the manual operation member is a case member 50 configured to surround the lead in a cylindrical shape with both ends open. A male screw is formed on the ring member 20, and a female screw is formed at a position in contact with the ring member 20 in the case member 50, so that the case member 50 and the ring member 20 are screwed together.

When the case member 50 is rotated in a first direction, the case member 50 is screwed with the ring member 20 to rotate the ring member in the first direction to adjust a position of the ring member 20 in the circumferential direction with respect to the lead, and when the case member 50 is rotated in a second direction opposite to the first direction, the screw coupling between the case member 50 and the ring member 20 is released to separate the case member 50.

In the description of the above embodiment, the case of using a lead and a lead system according to the present invention for deep brain stimulation has been described. However, in addition to the above-described embodiment, the lead and lead system according to the present invention may be widely used to relieve pain or treat diseases by applying electrical stimulation to body organs, such as spinal cord stimulation for pain relief, frontal nerve stimulation for dysuria, and vagus nerve stimulation for epilepsy or depression.

In the above, the present invention has been described with reference to embodiments, but the present invention is not limited to the embodiments and may be variously modified within the scope described in the claims, and these are also within the scope of the present invention.

The invention claimed is:

1. A lead implanted in a body to apply electrical stimulation to body organs, the lead comprising:
    an electrode wire having one end provided as an insertion portion to be inserted into a body and another end provided as an interface portion for connection with an external device;
    a first electrode in the insertion portion to transmit electrical stimulation to body organs;
    a second electrode on the interface portion to receive electrical stimulation applied from outside;
    a signal line that interconnects the first electrode and the second electrode to transmit electrical stimulation received by the second electrode to the first electrode; and
    a ring member disposed on the electrode wire that covers the first electrode and has an opening that exposes the first electrode in a portion of a circumferential direction, and is mounted on the electrode wire to be movable in a longitudinal or circumferential direction with respect to the electrode wire by an external force to adjust an exposure position of the first electrode through the opening,
    wherein the ring member is comprised of a plurality of ring members each comprised of an insulating material that prevents exposure of electrical stimulation therethrough and arranged adjacent to each other in a longitudinal direction at the insertion portion of the electrode wire,
    wherein each of the plurality of ring members is independently rotatable by at least one of a manual operation member or a controller to selectively adjust its position in the circumferential direction and the position of the opening to expose the first electrode through the opening of each of the plurality of ring members and to provide selective areas of the applied electrical stimulation from the first electrode through the openings.

2. The lead of claim 1, wherein each of the plurality of ring members is movable with respect to the electrode wire by the controller applying a magnetic force to attract and couple at least one ring member of the plurality of ring members to a portion of the controller and as the portion of the controller is one of moved or rotated in one of the longitudinal direction or the circumferential direction with respect to the electrode wire the at least one ring member is moved or rotated in the direction.

3. The lead of claim 1, wherein a gap between the openings of each of the plurality of ring members is adjusted by an external force applied to the manual operation member.

4. The lead of claim 1, wherein the first electrode extends obliquely along an outer surface of the electrode wire in the insertion portion.

5. The lead of claim 1, wherein a plurality of first electrodes is arranged in a form of point electrodes on an outer surface of the electrode wire in the insertion portion.

6. A lead system implanted in a body to apply electrical stimulation to body organs, the lead system comprising:
  a main processor connected to an external device for communication and control;
  one or more leads implanted in a body to apply electrical stimulation to body organs;
  an electrode clamp for electrical connection with the lead; and
  at least one of a manual operation member configured to be manually operated by an operator or a controller driven according to a control signal from the main processor, the manual operation member and the controller operable to insert, remove, or rotate the lead,
  wherein the lead comprises:
  an electrode wire having one end provided as an insertion portion to be inserted into a body and the other end provided as an interface portion for connection with an external device;
  a plurality of first electrodes in the insertion portion to transmit electrical stimulation to body organs;
  a plurality of second electrodes on the interface portion to receive electrical stimulation applied from outside;
  a plurality of signal lines that interconnect the first electrodes and the second electrode respectively to transmit electrical stimulation received by the second electrode to the first electrode;
  a ring member comprised of an insulating material that prevents exposure of electrical stimulation therethrough, that is disposed on the electrode wire to cover the first electrode, having an opening that exposes the first electrode in a portion of a circumferential direction, and being mounted on the electrode wire to be movable in a longitudinal or circumferential direction with respect to the electrode wire by an external force applied by the manual operation member or the controller to adjust an exposure position of the first electrode through the opening; and
  a guide wire inserted into an inner space of the electrode wire to support the electrode wire when the electrode wire is inserted into a brain region,
  wherein the ring member is comprised of a plurality of ring members arranged adjacent to each other in a longitudinal direction at the insertion portion of the electrode wire,
  wherein each of the plurality of ring members is independently rotatable by the manual operation member or the controller to selectively adjust its position in the circumferential direction and the position of the opening to expose the first electrode through the opening of each of the plurality of ring members and to provide selective areas of the applied electrical stimulation from the first electrode through the openings.

7. The lead system of claim 6, wherein the controller comprises:
  a driving element, including a linear motor and a rotary motor, driven according to a control signal from the main processor; and
  an operation key driven in an extension direction and a circumferential direction of the lead by the driving element, one end disposed adjacent to the ring member, and having a magnetic force,
  wherein the one end of the operation key is magnetized by application of electric power to apply a magnetic force to at least one of the plurality of ring members to at least one of move or rotate the ring member as the operation key is moved or rotated.

8. The lead system of claim 7, wherein the operation key is at a position of the guide wire of the lead, and is arranged to be inserted into the position of the guide wire in a state in which the guide wire is removed.

9. The lead system of claim 6, wherein the manual operation member comprises:
  a main body extending in a longitudinal direction of the lead;
  a mobile clamp provided on an upper end of the main body and applied with an operating force by an operator; and
  a press element that is expanded by the operating force applied to the mobile clamp,
  wherein the press element is arranged between openings of the ring member and expanded by the operating force to expand the openings.

10. The lead system of claim 6, wherein the manual operation member is a case member, coupling the plurality of ring members, configured to surround the lead in a cylindrical shape with both ends open,
  wherein a male screw is formed on each of the plurality of ring members, and a female screw is formed at a position in contact with each of the ring members in the case member, so that the case member and the ring members are screwed together.

11. The lead system of claim 10, wherein, when the case member is rotated in a first direction, the case member is screwed with the plurality of ring members to rotate each of the ring members in the first direction to adjust a position of the ring members in the circumferential direction with respect to the lead, and when the case member is rotated in a second direction opposite to the first direction, the screw coupling between the case member and the plurality of ring members is released to separate the case member.

* * * * *